(12) United States Patent
Lamango

(10) Patent No.: US 8,592,173 B2
(45) Date of Patent: *Nov. 26, 2013

(54) CANCER DIAGNOSIS BY MEASURING POLYISOPRENYLATED METHYLATED PROTEIN METHYL ESTERASE ACTIVITY

(75) Inventor: Nazarius Saah Lamango, Tallahassee, FL (US)

(73) Assignee: Florida Agricultural and Mechanical University, Tallahassee, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/290,363

(22) Filed: Nov. 7, 2011

(65) Prior Publication Data

US 2013/0084573 A1 Apr. 4, 2013

Related U.S. Application Data

(63) Continuation-in-part of application No. 13/012,942, filed on Jan. 25, 2011, now Pat. No. 8,053,307.

(51) Int. Cl.
*C12Q 1/44* (2006.01)

(52) U.S. Cl.
USPC .......................................................... 435/19

(58) Field of Classification Search
USPC .......................................................... 435/19
See application file for complete search history.

(56) References Cited

U.S. PATENT DOCUMENTS

| | | | |
|---|---|---|---|
| 5,202,456 A | 4/1993 | Rando | |
| 5,574,025 A | 11/1996 | Anthony et al. | |
| 5,705,528 A | 1/1998 | Kloog | |
| 6,372,793 B1 | 4/2002 | Lamango et al. | |
| 7,897,604 B2* | 3/2011 | Lamango | 514/252.13 |
| 2009/0253640 A1* | 10/2009 | Lamango | 514/18 |

OTHER PUBLICATIONS

Anderegg et al., "Structure of *Saccharomyces Cerevusuae* Mating Hormone A-Factor, Identification of S-Farnesyl Cysteine as a Structural Component", J Biology Chemistry, 263:18236-18240 (1988).
Anderson et al., "Purification, Functional Reconstitution and Characterization of the *Saccharomyces Cerevisiae* Isoprenylcysteine Carboxylmethyltransferase Ste14p", J Biology Chemistry, 280:7336-7345 (2005).
Ascherio et al, "Pesticide Exposure and Risk for Parkinson's Disease", Ann Neural 60:197-203 (2006).
Becker et al., "Synthesis and Structure-Activity Relationships of Beta-and Alpha-Piperidine Sulfone Hydroxamic Acid Matrix Metalloproteinase Inhibitors with Oral Antitumor Efficacy", J Med Chem, 48:6713-6730 (2005).
Bergo et al., "Isoprenylcysteine Carboxyl Methyltransferase Deficiency in Mice", J Biology Chemistry, 276:5481-5845 (2001).
Bifulco, "Rote of the Isoprenoid Pathway in ras Transforming Activity, Cytoskeleton Organization, Cell Proliferation and Apoptosis", Life Sciences, 77:1740-1749 (2005).
Calero et al., "*Saccharomyces Cerevisiae* Pra1p/Yip3p Interacts with Yip1p and Rab Proteins", Biochem Biophys Res Commun, 290:676-681(2002).
Capdevila et al., "Pancreatic Exocrine Secretion is Blocked by Inhibitors of Methylation", Arch Biochem Biophys 345:47-55 (1997).
Chen et at, "G Protein β2 Subunit Interacts Directly with Neuropathy Target Esterase and Regulates its Activity", Intl J Biochem & Cell Biology, 39:124-132 (2007).
Cohen et al., "Inhibitors of Prenylation of Ras and Other G-Proteins and Their Application as Therapeutics", Biochem Pharmacol, 60:1061-1068 (2000).
Costa, "Current Issues in Organophosphate Toxicology", Clin Chem Acta, 366:1-13 (2006).
Dietrich et al., "Isoprenylation of the G Protein Gamma Subunit is Both Necessary and Sufficient for Beta Gamma Dimmer-mediated Stimulation of Phospholipase", C Biochemistry, 35:15174-15182 (1996).
Ding et al., "Farnesyl-L-Cysteine Analogs Can Inhibit or Initiate Superoxide Release by Human Neutrophils", J Biol Chem, 269:16837-16844 (1994).
Dolence et al., "A Mechanism for Posttranslational Modifications of Proteins by Yeast Protein Farneysltransferase", Proc National Acad Sci, 92:5008-5011 (1995).
Erhardt et al., "Ras and Relatives—Job Sharing and Networking Keep an Old Family Together", Exp Hematol 30:1089-1106 (2002).
Glynn, "Neuroapthy Target Esterase and Phospholipids Deacylation", Biochim Biophys Acta, 1736:87-93 (2005).
Grosser et al., "C-Terminal Binding Domain of Rho GDP-Dissociation Inhibitor Directs N-Terminal Inhibitory Peptide to GTPases", Nature 387:814-819 (1997).
Khosravi-Far et al., "Ras (CXXX) and Rab (CC/CXC) Prenylation Signal Sequences are Unique and Functionally Distinct", J Biol Chem 267:24363-24368 (1992).
Kloog et al., "Prenyl-Binding Domains: Potential Targets for Ras Inhibitors and Anti-Cancer Drugs", Seminars in Cancer Biology 14:253-261 (2004).
Lamango et al., "Quantification of S-Adenosylmethionine-Induced Tremors: A Possible Tremor Model for Parkinson's Disease", Pharma Biochem and Behavior, 65(3):523-529 (2000).
Lamango, "Liver Prenylated Methylated Protein Methyl Esterase is an Organophosphate-Sensitive Enzyme", J Biochem Molecular Toxicology, 19(5):347-357 (2005).
Lebowitz et al., "Farnesyltransferase Inhibitors Alter the Prenylation and Growth-Stimulating Function of RhoB", J Blot Chem, 272:15591-15594 (1997).
Ma et al., "Mechanistic Studies an Human Platelet Isoprenylated Protein Methyltransferase: Farnesylcysteine Analogs Block Platelet Aggregation Without Inhibiting the Methyltransferase", Biochem, 33:5414-5420 (1994).

(Continued)

Primary Examiner — Maryam Monshipouri
(74) Attorney, Agent, or Firm — Parks IP Law LLC; Collen A. Beard, Esq.

(57) ABSTRACT

Methods for cancer diagnosis, making decisions on appropriate cancer treatment, awareness of a predisposition to cancer and potential cancer prevention, and monitoring of cancer therapy by measuring the activity of PMPMEase.

16 Claims, 5 Drawing Sheets

(56) References Cited

OTHER PUBLICATIONS

Marom et al., "Selective Inhibition of Ras-Dependent Cell Growth by Farnesylthiosalisylic Acid", J Biol Chem, 270:22263-22270 (1995).

Martincic et al., "Isolation and Characterization of a Dual Prenylated Rab and VAMP2 Receptor", J Biol Chem, 272:26991-26998 (1997).

McTaggart, "Isoprenylated Proteins", Cell Mol Life Sci, 63:255-267 (2006).

Morris et al., "Physiological Regulation of G Protein-Linked Signaling", Physiol Rev, 79:1373-1430 (1999).

Muhlig-Versen et al., "Loss of Swiss Cheese/Neuropathy Target Esterase Activity Causes Disruption of Phosphatidylcholine Homeostasis and Neuronal and Glial Death in Adult Drosophilia", J Neurosci, 25:2865-2873 (2005).

Muller-Vahl et al., "Transient Severe Parkinsonism After Acute Organophosphate Poisoning", J Neural Neurosurg Psychiatry, 66:253-254 (1999).

Myung at al., "Role of Isoprenoid Lipids on the Heterotrimeric G Protein Gamma Subunit in Determining Effector Activation", J Biel Chem, 274:16595-16603 (1999).

Parish at al., "Isoprenylation/Methylation of Proteins Enhances Membrane Association by a Hydrophobic Mechanism", Biochemistry, 35:8473-8477 (1996).

Pereira-Leal et al., "Prenylation of Rab GTPases: Molecular Mechanisms and Involvements in Genetic Disease", FEBS Letters, 498:197-200 (2001).

Perez-Sala et al., "Prenylated Protein Methyltransferases do not Distinguish Between Farnesylated and Geranylgeranylated Substrates", Biochem J, 284:835-840 (1992).

Regazzi at al., "Prenylcysteine Analogs Mimicking the C-Terminus of GTP-Binding Proteins Stimulate Exocytosis from Permeabilized HIT-T15 Cells: Comparison with the Effect of Rab3AL Peptide", Biochim Biophys Acta, 1268:269-278 (1995).

Roskoski, Jr., "Protein Prenylation: A Pivotal Posttranslational Process", Biochem and Biophys Res Comm, 303:1-7 (2003).

Seabra et al., "Rab GTPases, Intercellular Traffic and Disease", Trends in Mol Med, 8(1):23-30 (2002).

Seymour, "Novel Anti-Cancer Agents in Development: Exciting Prospects and New Challenges", Cancer Treat Rev, 25:301-312 (1999).

Shields et al., "Understanding Ras: 'it ain't over 'til it's over'", Trends Cell Biol, 10:147-154 (2000).

Lamango et al., "Farnesyl-L-Cysteine Analogs Block SAM-Induced Parkinson's Disease-Like Symptoms in Rats", Pharm Bio and Behavior, 66(1):841-849 (2000).

* cited by examiner

CANCER DIAGNOSIS BY MEASURING POLYISOPRENYLATED METHYLATED PROTEIN METHYL ESTERASE ACTIVITY

CROSS REFERENCE TO RELATED APPLICATION

This application is a continuation-in-part of U.S. application Ser. No. 13/012,942, filed Jan. 25, 2011 now U.S. Pat. No. 8,053,207 the entirety of which is incorporated herein by reference.

STATEMENT REGARDING FEDERALLY SPONSORED RESEARCH OR DEVELOPMENT

This invention was made with government support under NIH/NIGMS/SCORE grant GM 08111-35 and Pharmaceutical Research Center NIH/NCRR grant G12 RR0 3020. The government has certain rights in the invention.

BACKGROUND OF THE INVENTION

It has been discovered that the activity of a particular enzyme, polyisoprenylated methylated protein methyl esterase (PMPMEase which is also known as human carboxylesterase 1 or hCE1), is elevated in certain cancers, such as in breast cancer. The present invention is methods for the diagnosis and treatment of cancer, by measuring the activity of the enzyme PMPMEase.

Breast cancer is not one disease but several different diseases. Three types of breast cancer are estrogen receptor (ER)-positive breast cancer, progesterone receptor (PR)-positive breast cancer (together termed hormone receptor positive breast cancer), and human epidermal growth factor receptor 2 (HER2)-positive breast cancer (triple positive breast cancer refers to the presence of ER, PR, and HER2 receptors). These subtypes of breast cancer are generally diagnosed based upon the presence, or lack of these three receptors. In addition, the most successful treatments for breast cancer target these receptors. Another type of breast cancer is called triple negative breast cancer, since none of these three receptors are found in the offending tumor. Because of its triple negative status, triple negative tumors generally do not respond to receptor targeted treatments. Depending on the stage of its diagnosis, triple negative breast cancer can be particularly aggressive, and more likely to recur than other subtypes of breast cancer. Although it cannot be treated with receptor targeted treatments it is commonly receptive to chemotherapy. The lack of targets for treating triple negative breast cancer implies that more research needs to be pursued to find what drives this form of cancer as well as other cancers of unknown etiologies.

Proper diagnosis of the type of breast cancer is essential for proper treatment.

Protein polyisoprenylation and subsequent methylation are essential modifications on a significant proportion of eukaryotic proteins. The modifications are a series of post-translational modifications involving motifs such as -CAAX wherein C is cysteine, A is any aliphatic amino acid, and X is any amino acid whose nature specifies either farnesylation or geranylgeranylation. The modifications include polyisoprenylation of the cysteine of the -CAAX motif (on the sulfur), proteolysis of the carboxyl-terminal three amino acids (AAX), and methylation of the carboxyl group of the cysteine. In the polyisoprenylation step, a 15 carbon (trans, trans-farnesyl) or 20 carbon (all trans-geranylgeranyl) hydrocarbon group is covalently added to the protein.

The only reversible step in the process is the last step, methylation. Two enzymes mediate this final state of polyisoprenylated proteins. Polyisoprenylated protein methyl transferase (PPMTase), also known as isoprenyl carboxylmethyl transferase (ICMT), transfers a methyl group from S-adenosyl-L-methionine (SAM) to the C-terminal —COO$^-$ to form the methylated polyisoprenylated protein. PPMTase is essential to the developing embryo; knockout mice lacking PPMTase activity do not survive through mid-gestation. The second of the two enzymes is polyisoprenylated methylated protein methyl esterase (PMPMEase), which hydrolyzes the methyl esters of polyisoprenylated proteins to form the original proteins with free —COO$^-$ groups.

PPMTase and PMPMEase counterbalance the effects of each other. It is conceivable that the methylated and demethylated forms of prenylated proteins may be variously preferred for functional interactions by different protein targets, thus rendering PPMTase and PMPMEase very important moderators of polyisoprenylated protein function. Accordingly, manipulation of these enzymes should render significant effects on many cellular functions.

PMPMEase, through its possible regulation of the functions of various types of polyisoprenylated proteins, may exert profound effects on various intracellular events and consequently on animal physiology. Proteins such as the G-gamma subunits of heterotrimeric G-proteins of the G-protein coupled receptors, nuclear lamins, and guanine nucleotide-binding proteins such as Ras are polyisoprenylated and undergo methylation. These proteins mediate processes ranging from neurotransmitter signaling, cytoskeletal and intracellular transportation functions, cell proliferation, differentiation, and apoptosis. It could be inferred from this that aberrant levels of PMPMEase activity would be expressed through disease states such as cancers, neurodegenerative, and neuropsychiatric disorders. In fact, hyperactivity of monomeric G-proteins is implicated in an estimated 30% of cancers. Ghobrial I M, et al., Hematol. Oncol. Clin North Am. 2002, 16(5):1065-1088.

PMPMEase is inhibited by millimolar concentrations of the anticancer drugs tamoxifen and cyclophosphamide as well as by micromolar concentrations of the chemopreventive compound curcumin and polyunsaturated fatty acids such as arachidonic acid (AA). Prostaglandin (PG) $A_2$ was 63-fold less potent than AA while $PGE_2$ did not inhibit PMPMEase at 1 mM. AA's effects on cell death coupled with the expression of COX-2 in various tumors and tumor cell lines may imply that COX-2 converts AA into PGs, thereby destroying AA's ability to effectively inhibit PMPMEase and regulate cell growth. These results also show that balanced PMPMEase activity may be critical for normal cell viability.

It is an object of the invention to provide a method for detecting cancer which involves measuring the activity of the enzyme PMPMEase. While breast cancer is used as an exemplary embodiment herein, the invention is not limited to breast cancer.

SUMMARY OF THE INVENTION

The present invention is methods for the diagnosis, prediction, and treatment of cancer, based upon the activity of the enzyme PMPMEase.

PMPMEase activity is elevated in cancerous tissue compared to surrounding non cancerous tissue. Accordingly, an increase in PMPMEase activity is a marker for the presence of cancer, or a predisposition to cancer. Measurement of PMPMEase activity can therefore be the basis for cancer diagnosis, decisions on appropriate cancer treatment, awareness of a predisposition to cancer and potential cancer prevention, and monitoring of cancer therapy.

In one embodiment, the invention is a method of cancer diagnosis or prediction (together termed "detection") including the steps 1) gathering a biological sample from a subject and 2) assaying the biological sample for PMPMEase activity. In a third step the PMPMEase activity in the biological sample is compared to PMPMEase activity in a control biological sample. In some preferred embodiments the biological sample is from a breast tumor. In other preferred embodiments, the biological sample is from lung, pancreatic, or ovarian cancerous tissue.

DETAILED DESCRIPTION OF THE INVENTION

Figure 1:
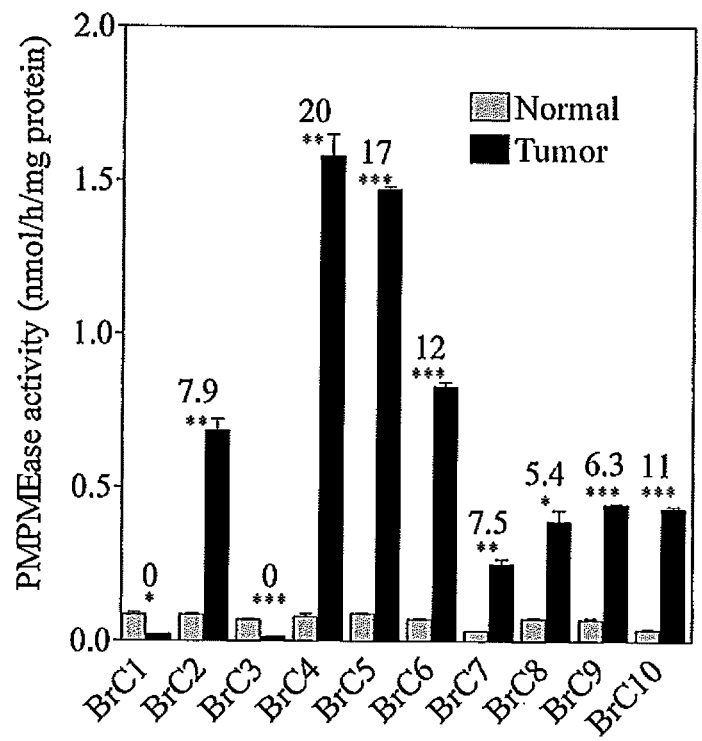
FIG. 1 is a chart showing PMPMEase activity in nmol/h/mg protein. Breast tumor samples are shown as solid black bars with corresponding normal breast tissue as gray bars. Each bar represents the mean±SEM, N=3. The number above each pair of bars represents the fold increase in the activity in the tumor sample over that of the normal adjacent tissue. The significance between the tumors and adjacent normal tissues were calculated using paired t-tests and *,  and * denote P-values equal to or less than 0.05, 0.01 and 0.001, respectively.

PMPMEase activity is elevated in cancerous tissue compared to surrounding non cancerous tissue. Accordingly, an increase in PMPMEase activity is a marker for the presence of cancer, or a predisposition to cancer.

In one embodiment, the invention is a method of cancer detection including the steps 1) gathering a biological sample from a subject and 2) assaying the biological sample for PMPMEase activity. In a third step the PMPMEase activity in the biological sample is compared to PMPMEase activity in a control biological sample.

Cancer as used herein means the presence of cells possessing characteristics typical of cancer causing cells, such as uncontrolled proliferation, immortality, metastatic potential, rapid growth and proliferation rate, and certain characteristic morphological features. Often, cancer cells will be in the form of a tumor, but such cells may exist alone within an animal, or may be a non-tumorigenic cancer cell, such as a leukemia cell. Cancers include, but are not limited to breast cancer, lung cancer, bronchus cancer, colorectal cancer, prostate cancer, pancreas cancer, stomach cancer, ovarian cancer, urinary bladder cancer, brain or central nervous system cancer, peripheral nervous system cancer, esophageal cancer, cervical cancer, a melanoma, uterine or endometrial cancer, cancer of the oral cavity or pharynx, liver cancer, kidney cancer, testis cancer, biliary tract cancer, small bowel or appendix cancer, salivary gland cancer, thyroid gland cancer, adrenal gland cancer, osteosarcoma, and a chondrosarcoma. While the invention is particularly shown herein as applicable for detection of breast, lung, pancreatic, and ovarian cancers it is applicable to other cancers as well. In particular, it is likely that other cancers such as, but not limited to, melanoma, prostate, liver, colon, kidney, and brain cancers also have elevated levels of PMPMEase activity.

In another embodiment the invention is a method of preventing development or further development of cancer. If a subject is found to have elevated levels of PMPMEase activity, indicating a predisposition towards or presence of cancer, measures can be taken to prevent further development of the cancer. An appropriate cancer therapy depends upon the type and extent of the cancer and can be selected from chemotherapy, radiation therapy, surgery, antihormone therapy, receptor-targeted therapy, and immunotherapy. Other therapies include changes in diet and exercise. For example, in those cases where the PMPMEase activities are elevated, the consumption of foods rich in natural PMPMEase inhibitors such as polyunsaturated free fatty acids and curcumin may be recommended as an alternative remedy or for prevention of relapse. Specifically designed high affinity inhibitors of PMPMEase appropriately developed as drugs will be more suitable for targeting cancers with elevated PMPMEase activities.

In one preferred embodiment, the method is specific for detection of triple negative breast cancer. PMPMEase has particularly high activity in triple negative breast cancer. This is a particularly striking result since triple negative breast cancer has heretofore been difficult to treat. Although chemotherapy is a treatment option for triple negative breast cancer, the lack of a specific drug target implies that response to therapy is less than for the hormone-driven breast cancers which have more specific targeted therapeutic options and consequently better prognoses.

In another embodiment the invention is a method of screening foods, drugs, and other active agents for their ability to prevent or treat cancer by measuring their effect on PMPMEase activity.

In still another embodiment, the invention is the development of inhibitors targeted towards the suppression of PMPMEase activity to the level found in normal tissues.

In another embodiment, the invention is useful for treatment monitoring by measuring PMPMEase levels as a treatment progresses to determine its effectiveness.

PMPMEase activity can be measured in a number of ways that will be understood by those skilled in the art. Generally, enzyme activity is measured by measuring either the consumption of a substrate or the production of a product over time. For example, the biological sample can be incubated with a known PMPMEase substrate for a period of time, after which time the sample is assayed for the known enzymatic product.

The first step in the method is to collect the biological sample. This can be done through means well known in the art, by removing a sample of cells from the subject, but can also be accomplished by using previously isolated cells, or by performing the enzyme assay in vivo. The biological sample could alternatively be non-cellular biological material, such as non-cellular fractions of blood, saliva, or urine that can be used to measure PMPMEase activity. Preferred biological samples include tissue biopsies, scrapes (e.g. buccal scrapes), whole blood, plasma, serum, urine, saliva, cell culture, or cerebrospinal fluids. All of these are referred to herein as the biological sample or cells unless otherwise noted.

Often a control biological sample will also be obtained from the subject. This is a sample of biological material representative of healthy, cancer-free cells, preferably cells or tissue obtained from the same location of the subject. A control sample can also refer to an established level of PMPMEase activity representative of the cancer-free cells, which has been previously established based on measurements from normal, cancer-free cells.

The biological sample and control sample may need to be processed prior to the assay for PMPMEase activity. For example, it may be desirable to weigh and sonicate, homogenize or lyse the cells or tissues in a suitable buffer of pH at around 7.4 prior to incubation with the substrate. After incubation of the tissue extract/sample at or about 37° C. for a suitable amount of time, the reaction can be stopped by introducing conditions that denature proteins such as by heating or preferably adding a reagent that denatures the enzyme. Such reagents include, but are not limited to methanol and ethanol. Reagents such as acids or bases that may cause the ester bonds to break would generally be unsuitable. After centrifuging the stopped reactions to remove particulate matter, the supernatant liquids can then be analyzed.

The general PMPMEase reaction is shown as:

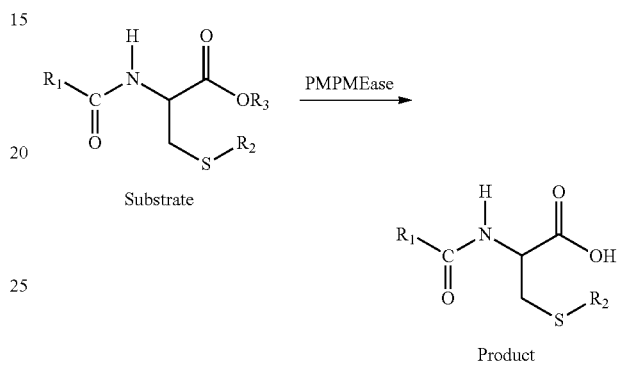

A number of PMPMEase substrates can be used to assay PMPMEase activity. In order for PMPMEase to be selective for the substrate and to avoid interference from other esterases, $R_2$ is a polyisoprenyl group such as a trans, trans-farnesyl or all trans-geranylgeranyl group. Other hydrophobic groups can be used for $R_2$ with varying degrees of selectivity for PMPMEase. $R_3$ is naturally a methyl group as found in polyisoprenylated proteins and for the purposes of detecting the enzyme activity, a methyl as $R_3$ will serve the purpose although ethyl and other usually hydrophobic groups will still be functional. $R_1$ can be very diverse in chemical structure and application. For the purpose of sensitivity, groups that interact strongly with light such as fluorescent or chromophoric (light absorbing) groups will be most effective. The substrates can also be adapted for other detection methods such as radiolabeling.

A preferred substrate is L-N-(4-nitrobenzoyl)-S-trans, trans-farnesyl-cysteine methyl ester (RD-PNB). Other substrates that could be used are L-N-(2-nitrobenzoyl)-S-trans, trans-farnesyl-cysteine methyl ester, L-N-(3-nitrobenzoyl)-S-trans,trans-farnesyl-cysteine methyl ester, L-N-(benzoyl)-S-trans,trans-farnesyl-cysteine methyl ester, L-N-(hippuryl)-S-trans,trans-farnesyl-cysteine methyl ester or L-N-(benzoyl-glycyl)-S-trans,trans-farnesyl-cysteine methyl ester (BzGFCM) and their geranyl and geranylgeranyl analogs. The structures of BzGFCM and RD-PNB are shown below.

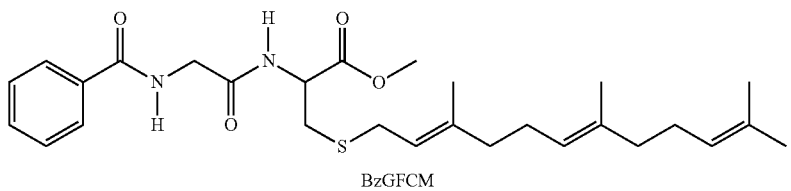

BzGFCM

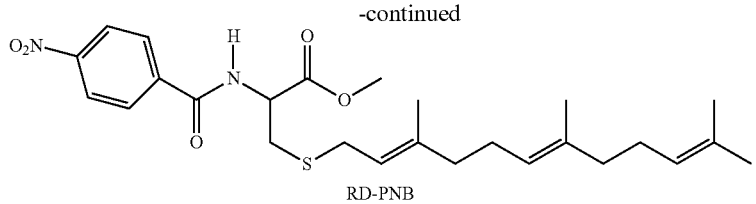
RD-PNB

Once the biological sample is obtained and processed, if desired, it is assayed for PMPMEase activity. The amount of PMPMEase activity in the tumor biological sample can be compared against the PMPMEase activity in normal control tissue. Preferably the difference between the increased level of PMPMEase activity in the biological sample and the level of PMPMEase activity in the control sample is statistically significant. Ethylenediaminetetraacetic acid (EDTA) can be included in the assay buffer to inactivate matrix metalloproteases.

In one embodiment, the amount of product formed is determined using reversed-phase high performance liquid chromatography with ultraviolet detection (HPLC-UV). The amounts of product formed will then be computed with the aid of a standard plot of amount of product against ultraviolet absorption to determine the relative activities of PMPMEase in the biological samples in order to make a diagnosis.

Other means for measuring the product formation or substrate depletion include radioactively labeling the substrate. In such as a scenario, reversed-phase HPLC analysis with radiochromatographic detection or other chromatographic methods coupled with radioactivity detection methods can be used.

An increase in an enzyme's activity may be due to increased levels of the protein, a mutation that makes the protein more active (also called gain-of-function mutation to distinguish it from loss-of-function mutations that result in a less active protein), or the loss of a moderating factor such as a natural endogenous or exogenous inhibitor. Increased expression of enzyme can be monitored by quantifying the levels of messenger RNA (mRNA) using RT-PCR (less accurate) or levels of protein using ELISA and/or western blotting (WB) and/or immunohistochemistry (IH). ELISA, WB and IH—which involve the use of antibodies—can be jointly termed immunological methods and are more predictive of increased protein levels and/or activity than RT-PCR. Changes in protein activity that are due to mutations only but which do not affect gene regulation i.e. do not cause changes in mRNA and therefore protein synthesis cannot be detected by western blotting and ELISA. Loss of a moderating factor is also not detectable by WB and ELISA using antibodies directed at PMPMEase.

Changes in PMPMEase's activity due to any of the three factors above can be detected by the above discussed PMPMEase enzymatic assays. However, for some, perhaps a significant proportion of the cases, the increase in PMPMEase enzyme activity will be due to an increase in PMPMEase expression. Therefore, RT-PCR and the immunological methods for measuring increase in PMPMEase levels can also be used to predict increased PMPMEase activity. Because of the reasons stated above and the fact that proteins may be inactive due to denaturation and/or functional regulation, the true physiological impact of a protein can be most accurately evaluated using a functional assay of its activity.

The examples below serve to further illustrate the invention, to provide those of ordinary skill in the art with a complete disclosure and description of how the compounds, compositions, articles, devices, and/or methods claimed herein are made and evaluated, and are not intended to limit the scope of the invention. In the examples, unless expressly stated otherwise, amounts and percentages are by weight, temperature is in degrees Celsius or is at ambient temperature, and pressure is at or near atmospheric.

EXAMPLE 1

Breast Cancer Screening with PMPMEase Activity

Materials and Methods

Ten breast cancer tumor samples together with respective matching adjacent normal tissues were obtained from ProteoGenex (Culver City, Calif.). The specimens were from ten Caucasian women ranging from age 44 to 77 years. The ER, HER2 and progesterone receptor status for three of the ten samples was known. The sample BrC5 was triple negative, BrC7 was positive for estrogen and progesterone receptors and negative for HER2, and BrC10 was positive for HER2 only. The tissues were collected and surgically excised by certified medical pathologists at ProteoGenex and snap-frozen in liquid nitrogen within 30 min of surgery. All the samples were of stage IIIA with histological diagnoses of infiltrating ductal carcinomas. The samples and their characteristics are listed in Table 1.

The TNM Classification of Malignant Tumours (TNM) is a cancer staging system that describes the extent of cancer in a patient's body. T describes the size of the tumor and whether it has invaded nearby tissue and ranges from 0 to 4, N describes the degree of spread to regional lymph nodes and ranges from 0 to 3, and M describes presence of metastasis and is either 0 (no metastasis) or 1 (metastasis beyond regional lymph nodes).

TABLE 1

| ID | Grade | TNM | ER/PR/HER2 status |
|---|---|---|---|
| BrC1 | G2 | T2N2M0 | unknown |
| BrC2 | G3 | T2N2M0 | unknown |
| BrC3 | G2 | T2N2M0 | unknown |
| BrC4 | G3 | T2N2M0 | unknown |
| BrC5 | G3 | T3N1M0 | Triple negative |
| BrC6 | G2-G3 | T2N2M0 | unknown |
| BrC7 | G2 | T2N2M0 | ER(+)/PR(+) |
| BrC8 | G2 | T2N2M0 | unknown |
| BrC9 | G3 | T3N1M0 | unknown |
| BrC10 | G3 | T2N2M0 | HER2 (+) |

The substrate L-N-(4-nitrobenzoyl)-S-trans,trans-farnesyl-cysteine methyl ester (RD-PNB) was synthesized as described in Lamango, N. S. et al. (2009) TOEIJ 2, 12-27(1). This substrate is an adaptation of the PMPMEase substrates described in Lamango, N. S. (2005) J Biochem Mol Toxicol 19, 347-357 and Oboh, O. T. et al. (2008) J Biochem Mol Toxicol 22, 51-62.

The frozen tumor and adjacent matching controls were weighed and sonicated in ice-cold 100 mM Tris-HCl buffer, pH 7.4 containing 1 mM ethylenediaminetetraacetic acid (EDTA) (5× mass of tissue). Aliquots of the homogenates (95 μL) were incubated with the RD-PNB substrate (1 mM) at 37° C. for 3 h. The reactions were stopped by the addition of 200 μL methanol. After chilling them at −20° C. for at least 5 min, they were centrifuged at 5000×g for 5 min and the supernatants analyzed by reversed-phase HPLC with UV-detection at 260 nm as described in Lamango, N. S. et al. (2009) TOEIJ 2, 12-27(1). The amount of product formed was determined using a calibration plot of HPLC UV-peak areas for known amounts of product standards. The total protein in the homogenates was determined using the bicinchoninic acid method.

Results

Figure 2:
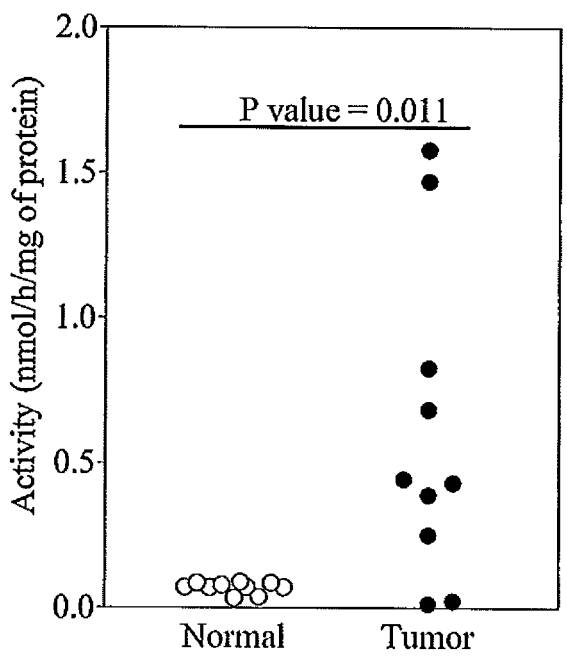
FIG. 2 is a chart of PMPMEase activity in nmollh/mg protein for breast tumor and normal breast tissue samples showing a P value of 0.011.
Figure 3:
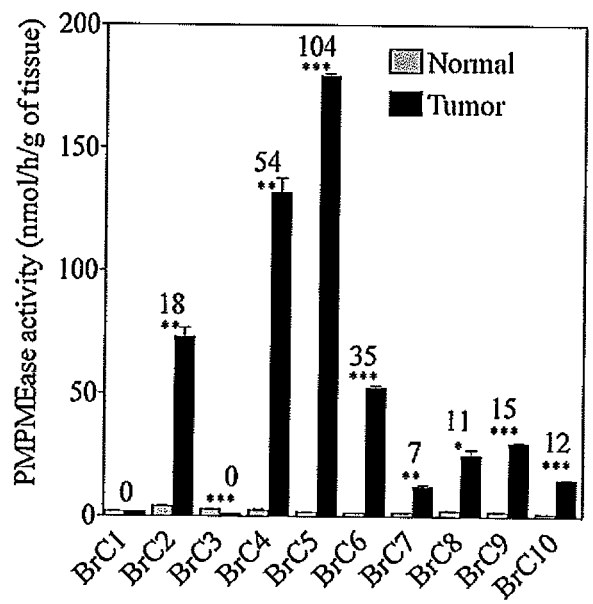
FIG. 3 is a chart showing PMPMEase activity in nmol/h/g of tissue fresh weight. Breast tumor samples are shown as solid black bars with corresponding normal breast tissue as gray bars. Each bar represents the mean±SEM, N=3. The number above each pair of bars represents the fold increase in the activity in the tumor sample over that of the normal adjacent tissue. The significance between the tumors and adjacent normal tissues were calculated using paired t-tests and *,  and * denote P-values equal to or less than 0.05, 0.01 and 0.001, respectively.
Figure 4:
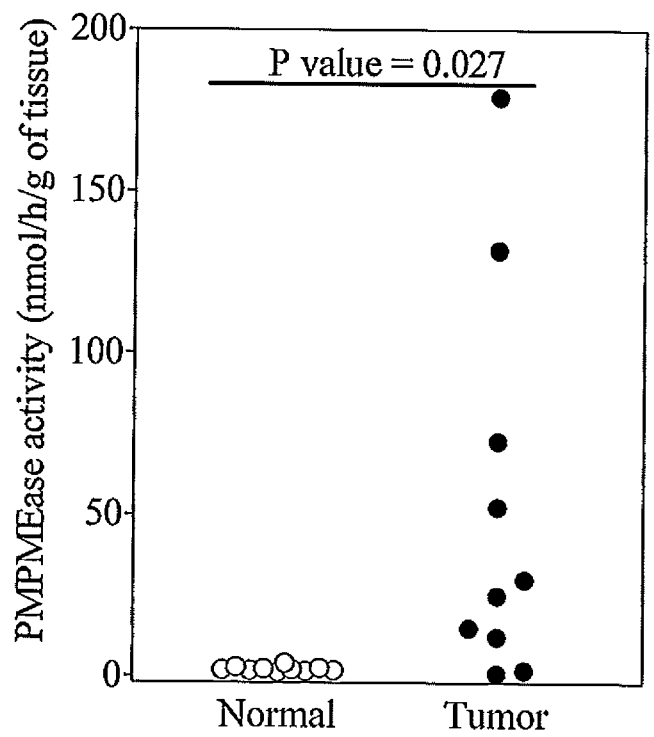
FIG. 4 is a chart of PMPMEase activity in mmol/h/g of tissue protein for breast tumor and normal breast tissue samples showing a P value of 0.027.

FIGS. 1 and 2 illustrate PMPMEase activity as nmol/h/mg protein and FIGS. 3 and 4 show activity as mnol/h/g of tissue. Significantly higher enzymatic activities were detected in the cancer samples compared to the respective controls. As shown in FIGS. 1 and 2, the activities ranged from 0.03 to 0.09 nmol/h/mg of protein with a mean and standard deviation of 0.07±019 for the normal group compared to a range of 0.01 to 1.6 mnol/h/mg of protein (mean and standard deviation of 0.61±0.54) for the tumor samples. This reflects an 8.7-fold increase in total protein-based PMPMEase specific activity.

When the samples were analyzed based on the weighed mass of tissue rather than the total protein (FIGS. 3 and 4), even larger differences were observed between the normal and the cancer tissues. These ranged from 1.29 to 3.98 (mean of 2.13) nmol/h/g of tissue for the control group and 0.76 to 179 (mean of 52.0) nmol/h/g of tissue for the cancer tissue. This reflects a 24.4-fold increase in PMPMEase activity in the cancer over the control tissues. As shown in FIGS. 1 and 3, significant increases in PMPMEase activity were noted in 8 out of the 10 cases studied. Eliminating the two cases that showed no increased PMPMEase activities from the analysis reveal 11.3- and 31-fold increases for the protein based and tissue weight specific activities, respectively. The increase in PMPMEase activity in the tumor versus the respective control tissues ranged from 5.4- to 20-fold when measured in terms of protein and 7- to 104-fold when measured against tissue weight.

Specific Samples

BrC5, known to be triple negative, shows the most enhanced PMPMEase activity when based on the weighed mass of tissue (FIG. 3) and second highest when based on total protein. BrC7 (ER and PR positive) and BrC10 (HER2 positive) show much less increased PMPMEase activity.

EXAMPLE 2

Further Analysis of Triple Negative BrC5

Figure 5:
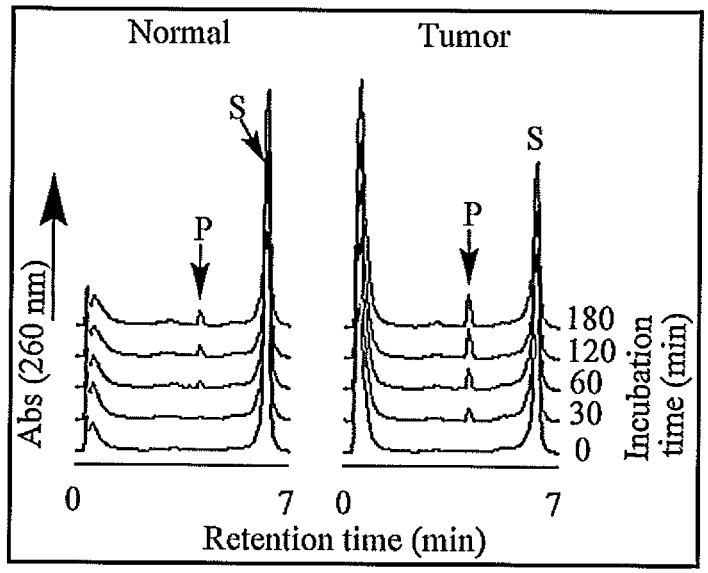
FIG. 5 shows product production and substrate depletion over time for normal breast tissue and breast tumor tissue.
Figure 6:
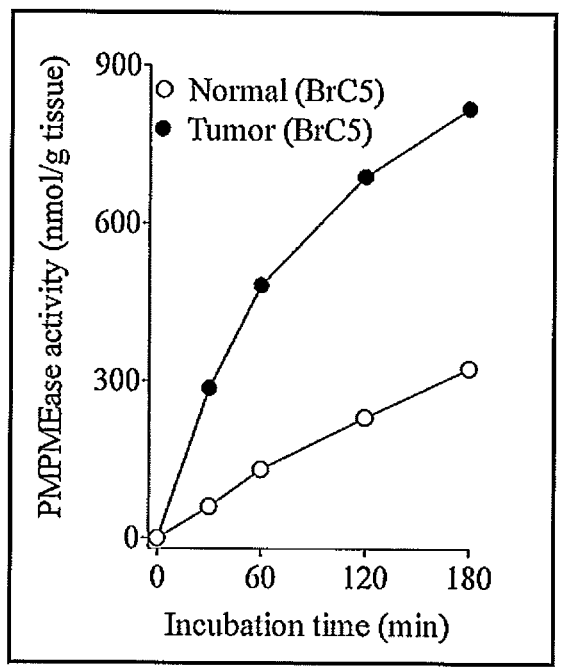
FIG. 6 charts the data shown in FIG. 5 as PMPMEase activity (nmol of product formed/g tissue) versus incubation time.

In a time-course analysis of substrate hydrolysis by BrC5 control and tumor tissues, 10 μL of homogenate was used instead of the 95 μL used in the initial screening of the samples. Briefly, 10 μL the homogenate was incubated with the RD-PNB substrate (1 mM) at 37° C. At the indicated time points, the reactions were stopped by the addition of 200 μL methanol. After chilling them at −20° C. for at least 5 min, they were centrifuged at 5000×g for 5 min and the supernatants analyzed by reversed-phase HPLC with UV-detection at 260 nm as described in Lamango, N. S. et al. (2009) *TOEIJ* 2, 12-27(1). The amounts of product formed were determined using a calibration plot of HPLC UV-peak areas for known amounts of product standards. As shown in FIGS. 5 and 6, the rate of formation of product was significantly higher in the tumor samples compared to the controls.

EXAMPLE 3

Breast Cancer Screening using Immunological Assay

Human tissue microarrays (TMAs) were supplied by and immunohistochemistry was conducted at US Biomax (Rockville, Md.). Two breast cancer TMAs consisted of 150 and 100 cores involving 75 and 50 cases. All the tissues were formalin-fixed, paraffin-embedded and mounted on positively charged SuperFrost Plus glass slides. The sections were all 5 μm thick and 1 or 1.5 μm in diameter. The cores were separated from each other by 0.25 mm.

Rabbit polyclonal antibody directed against PMPMEase (human carboxylesterase 1, hCE1) was obtained from Santa Cruz Biotechnology (Santa Cruz, Calif.). ImmPRESS Reagent anti-Rabbit Ig (peroxidase) reagent MP7401 and ImmPRESS Reagent anti-Rabbit Ig (peroxidase) reagent MP7405 were purchased from Vector Laboratories. DAB (DAKO Cytomation) was used as substrate chromogen. Antigen retrieval solution was purchased from DakoCytomation (Target Retrieval solution). The Antigen retrieval was performed before incubating with primary antibody.

The sections were deparaffinized in xylene and hydrated through a gradient ethanol series. These were rinsed in water for 5 min. These were then incubated in 3% hydrogen peroxide for 5 min to block endogenous peroxidase activity followed by two 5 min washes in water. The antigens were retrieved by simmering the sections in a microwave for 20 min in 1× antigen retrieval solution. These were allowed to cool to room temperature over a 15 min period before washing with three 5 min washes in PBST buffer. The sections were then incubated for 30 min with ready-to-use (2.5%) normal horse blocking serum. They were then incubated with diluted PMPMEase antibody (0.25 or 0.20 μg/mL). The slides were rinsed for three 5 min periods in buffer, incubated for 30 min in ImmPRESS reagent followed by a further 3×5 min washes in buffer. They were then exposed to the peroxidase substrate DAB solution. The sections were rinsed in tap water and counterstained in Hematoxylin QS (Vector Labs). These were then mounted using permanent mounting medium from Sigma (St. Louis, Mo.). The DAB substrate-chromogen stains the target antigen site dark brown while the hematoxylin stains the nuclei blue. The IHC-stained slides were scanned at 20× magnification.

Immunohistochemistry Scoring

The method used to score the PMPMEase immunoreactivity was adapted from that of Bremnes et al. (2002). The intensity of the staining was given a score of 0 (no staining), 1 (trace), 2 (weak), 3 (intermediate), 4 (strong), or 5 (very strong). The score of the staining intensity was then multiplied by the percentage of the immunoreactive tumor cells. The overall scores ranged between 0 and 500 with those between 1 and 100 described as trace, 101 to 200 as weak, 201 to 300 as intermediate, 301 to 400 as strong, and 401 to 500 as very strong. The evaluation and scoring was conducted without prior knowledge of the diagnosis of the individual samples on the TMAs.

Results

The immunological results show consistent immunoreactivity of PMPMEase in the tumors as opposed to the normal tissues or normal adjacent tissues (NAT). Although there was significant inter- and intra-slide variability in the intensities of the brown staining, which is indicative of the presence of PMPMEase, the staining was consistently more in tumor samples than in surrounding non-tumor tissues.

Figure 7:
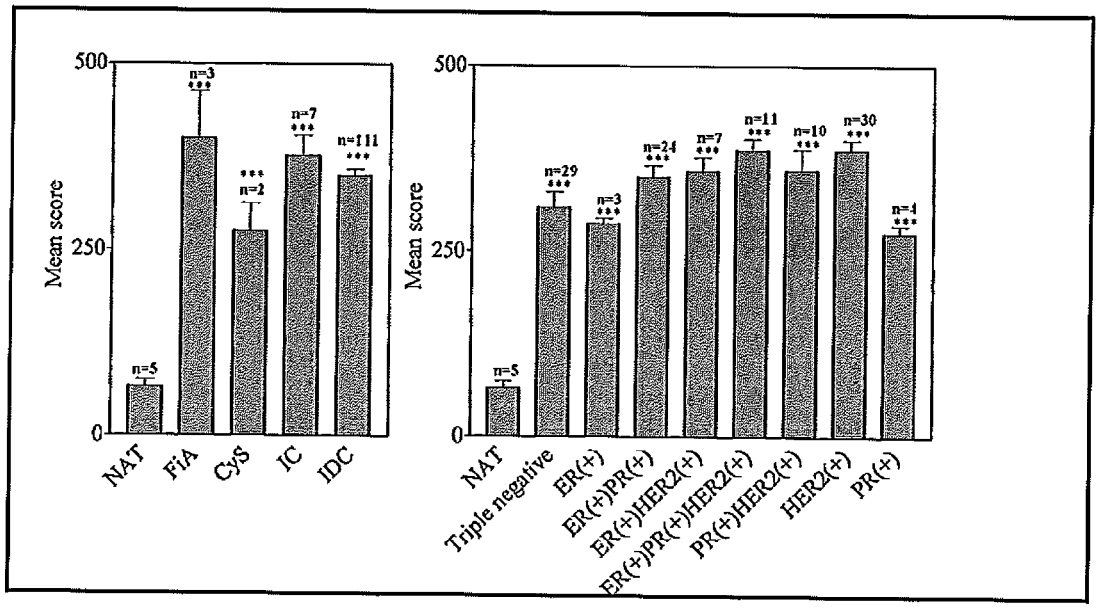
FIG. 7 is a bar graph illustrating immunoreactivity of various subtypes of breast cancer with PMPMEase antibody. The left panel shows breast cancer classification based on anatomical characteristics and the right panel illustrates classification based on genetic characteristics. The breast cancer subtypes are breast fibroadenoma (FiA), cystosarcoma (CyS), intraductal carcinoma (IC), and invasive ductal carcinoma (IDC) and NAT indicates normal adjacent tissues. Genetic classifications are positive for one or more of estrogen receptors [ER(+)], progesterone receptors [PR(+)], or human epidermal growth factor receptor type 2 receptors [HER2(+)]; negative for all three receptor types (triple negative breast cancer). The results are the means (±SEM, n values indicated above each bar are the number of cases used). *** indicates p<0.001 versus normal tissues compared by ANOVA followed by Newman-Keuls post test.

Specific subtypes of breast cancer were scored and graphed selectively. The results are shown in FIG. 7, with breast cancer classification based on anatomical characteristics (left panel) and genetic characteristics (right panel). These results show that PMPMEase is overexpressed in breast fibroadenoma (FiA), cystosarcoma (CyS), intraductal carcinoma (IC) and invasive ductal carcinoma (IDC) when compared to immunoreactivities in normal adjacent tissues (NAT) with relative scores±SEM of 400±63, 280±38, 380±27, 350±8 and 65±10, respectively. Similarly, breast tumors also showed overexpression of PMPMEase whether or not they were positive for one or more of estrogen receptors [ER(+)], progesterone receptors [PR(+)], or human epidermal growth factor receptor type 2 receptors [HER2(+)]. Tumors that were negative for all three receptor types (triple negative) also show an overexpression of PMPMEase. The mean scores±SEM of 310±21, 290±7, 350±15, 360±18, 390±14, 360±29, 390±13, 275±10 and 65±10 were recorded for TNBC, ER(+), ER(+)PR(+), ER(+)HER2(+), ER(+)PR(+)HER2(+), PR(2)HER(+), HER2(+), PR(+) and NAT, respectively. Tumors positive for HER2 alone or in conjunction with the other receptors consistently showed high intensities of PMPMEase immunoreactivity. The results shown are the means (±SEM, n values indicated above each bar are the number of cases used). *** p<0.001 versus normal tissues compared by ANOVA followed by Newman-Keuls post test.

EXAMPLE 4

Lung Cancer Screening using Immunological Assay

Figure 8:
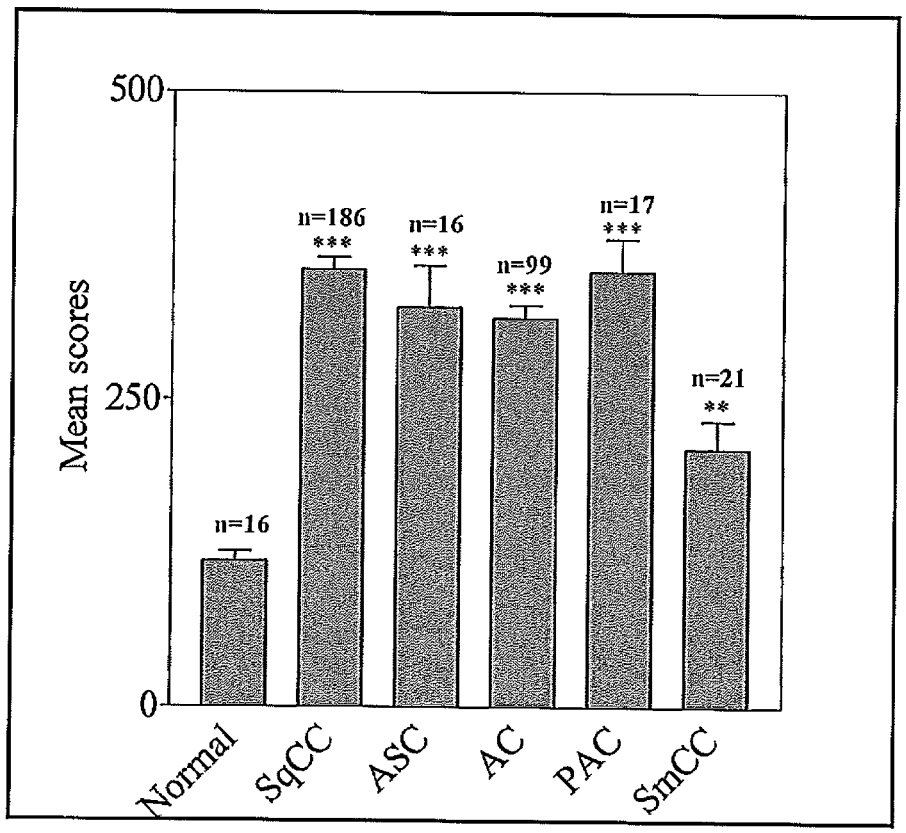
FIG. 8 is a bar graph illustrating PMPMEase immunoreactivities in various types of lung cancer: squamous cell carcinoma (SqCC), adenosquamous carcinoma (ASC), adenocarcinoma (AC), papillary adenocarcinoma (PAC), and small cell carcinoma (SmCC). The results are the means (±SEM, n values indicated above each bar are the number of cases used).  indicates p<0.01 and * indicates p<0.001 versus normal tissues compared by ANOVA followed by Newman-Keuls post test.

Lung cancer screening was performed following the above procedures. Two lung cancer TMAs were used consisting of a total of 416 cores involving 416 separate cases. FIG. 8 shows the results for relative PMPMEase immunoreactivities in various types of lung cancer and normal tissue. Significantly higher PMPMEase immunoreactivities with relative intensity scores±SEM of 360±10, 330±34, 320±10, 350±27 and 210±23 were observed in squamous cell carcinoma (SqCC), adenosquamous carcinoma (ASC), adenocarcinoma (AC), papillary adenocarcinoma (PAC), and small cell carcinoma (SmCC), respectively, compared to 120±8 for the staining of normal tissue sections.

EXAMPLE 5

Pancreatic Cancer Screening using Immunological Assay

Figure 9:
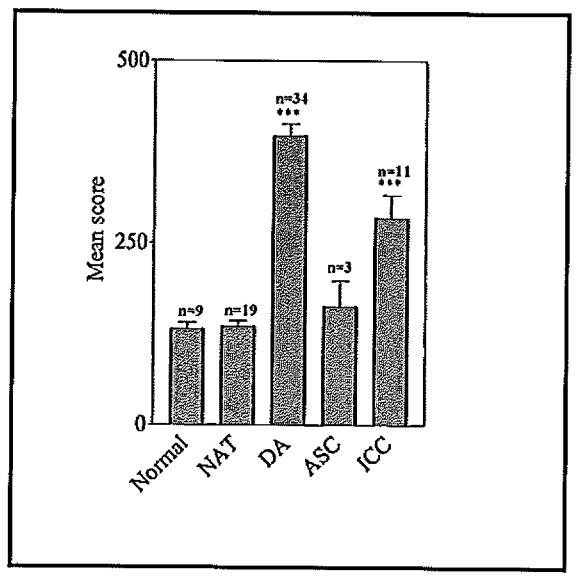
FIG. 9 is a bar graph showing relative PMPMEase immunoreactivities in various types of pancreatic cancer including duct adenocarcinoma (DA) and islet cell carcinoma (ICC) and compared with normal tissue sections or normal adjacent tissues (NAT).

Relative PMPMEase immunoreactivities were measured for various types of pancreatic cancer. TMAs were made from 208 cores of 101 and 104 cases and tested as described above and the results are shown in FIG. 9. PMPMEase immunoreactivities were scored as described above. Significantly higher PMPMEase immunoreactivities with intensity scores±SEM of 400±17 and 280±32 were observed for duct adenocarcinoma (DA) and islet cell carcinoma (ICC), compared to 130±9 and 130±8 staining for normal tissue sections and normal adjacent tissues (NAT), respectively.

EXAMPLE 6

Ovarian Cancer Screening using Immunological Assay

Figure 10:
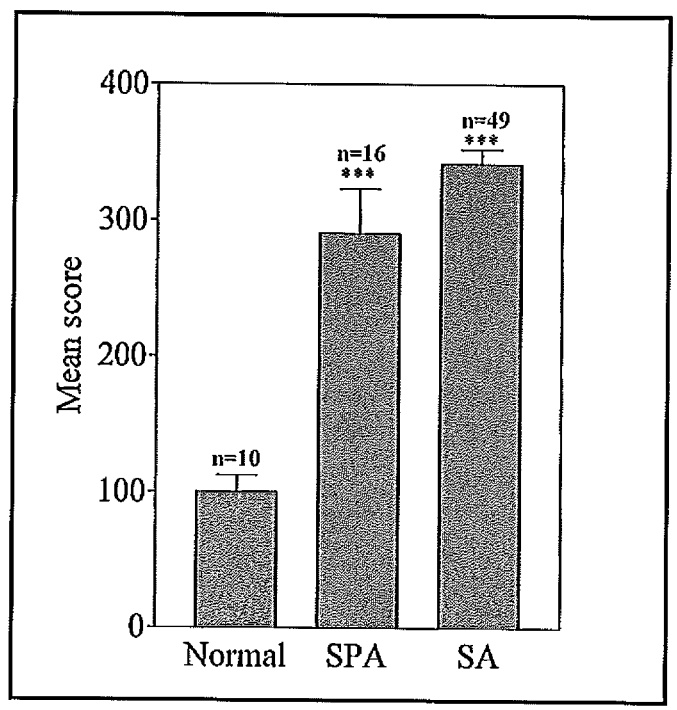
FIG. 10 shows relative PMPMEase immunoreactivities in ovarian cancer types serous papillary adenocarcinoma (SPA) and serous adenocarcinoma (SA), compared to normal tissues. The results are the means (±SEM, n values indicated above each bar are the number of cases used). *** is p<0.001 versus normal tissues compared by ANOVA followed by Newman-Keuls post test.

Relative PMPMEase immunoreactivities were measured for various types of ovarian cancer. TMAs were made from 208 cores of 101 and 104 cases. PMPMEase immunoreactivities were scored as described above and the results are shown in FIG. 10. Significantly higher PMPMEase immunoreactivities with relative intensity scores±SEM of 290±32 and 340±11 were observed in serous papillary adenocarcinoma (SPA) and in serous adenocarcinoma (SA), compared to staining 100±12 in normal tissues sections.

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. A method for detection of cancer in a biological sample comprising the step of assaying the biological sample for PMPMEase activity, wherein the biological sample is from lung, pancreatic, or ovarian tissue and the method is used to detect lung, pancreatic, or ovarian cancer.

2. The method of claim 1 wherein PMPMEase activity is PMPMEase enzymatic activity or level of PMPMEase.

3. The method of claim 1 further comprising the step of comparing the PMPMEase activity in the biological sample to PMPMEase activity in a non-cancerous biological sample.

4. The method of claim 2 wherein the level of PMPMEase is determined by an immunological method.

5. The method of claim 1 wherein the assaying step comprises incubating the biological sample with a PMPMEase substrate and measuring a change in concentration of the substrate or a product known to be produced by PMPMEase from the substrate.

6. The method of claim 5 wherein the substrate or product concentration is compared against a standard curve.

7. The method of claim 5 wherein the substrate is L-N-(4-nitrobenzoyl)-S-trans,trans-farnesyl-cysteine methyl ester (RD-PNB).

8. A method for detection of lung cancer in a biological sample comprising the step of assaying the biological sample for PMPMEase activity.

9. The method of claim 8 wherein PMPMEase activity is PMPMEase enzymatic activity or level of PMPMEase.

10. The method of claim 8 further comprising the step of comparing the PMPMEase activity in the biological sample to PMPMEase activity in a non-cancerous biological sample.

11. A method for detection of ovarian cancer in a biological sample comprising the step of assaying the biological sample for PMPMEase activity.

12. The method of claim 11 wherein PMPMEase activity is PMPMEase enzymatic activity or level of PMPMEase.

13. The method of claim 11 further comprising the step of comparing the PMPMEase activity in the biological sample to PMPMEase activity in a non-cancerous biological sample.

14. A method for detection of pancreatic cancer in a biological sample comprising the step of assaying the biological sample for PMPMEase activity.

15. The method of claim 11 wherein PMPMEase activity is PMPMEase enzymatic activity or level of PMPMEase.

16. The method of claim 11 further comprising the step of comparing the PMPMEase activity in the biological sample to PMPMEase activity in a non-cancerous biological sample.

* * * * *